United States Patent
Luger et al.

(10) Patent No.: US 10,610,573 B2
(45) Date of Patent: Apr. 7, 2020

(54) NDP-MSH FOR TREATMENT OF INFLAMMATORY AND/OR NEURODEGENERATIVE DISORDERS OF THE CENTRAL NERVOUS SYSTEM

(71) Applicant: Westfaelische Wilhelms—Universitaet Muenster, Muenster (DE)

(72) Inventors: Thomas A Luger, Muenster (DE); Karin Loser, Altenberge (DE)

(73) Assignee: WESTFAELISCHE WILHELMS-UNIVERSITAET MUENSTER, Muenster (DE)

( * ) Notice: Subject to any disclaimer, the term of this patent is extended or adjusted under 35 U.S.C. 154(b) by 0 days.

(21) Appl. No.: 14/909,604

(22) PCT Filed: Aug. 5, 2014

(86) PCT No.: PCT/EP2014/066816
§ 371 (c)(1),
(2) Date: Feb. 2, 2016

(87) PCT Pub. No.: WO2015/018827
PCT Pub. Date: Feb. 12, 2015

(65) Prior Publication Data
US 2016/0158322 A1 Jun. 9, 2016

(30) Foreign Application Priority Data

Aug. 5, 2013 (EP) .................................... 13003909
Aug. 9, 2013 (EP) .................................... 13179911

(51) Int. Cl.
*A61K 45/06* (2006.01)
*A61K 38/34* (2006.01)
*A61K 9/00* (2006.01)

(52) U.S. Cl.
CPC ............ *A61K 38/34* (2013.01); *A61K 9/0019* (2013.01); *A61K 45/06* (2013.01)

(58) Field of Classification Search
None
See application file for complete search history.

(56) References Cited

U.S. PATENT DOCUMENTS 5,674,839 A * 10/1997 Hruby .................. C07K 14/685
514/10.7
7,807,143 B2 10/2010 Brod

OTHER PUBLICATIONS

Brod et al., Ingested (oral) alpha-MSH inhibits acute EAE, 2008, Journal of Neuroimmunology 193:106-112.*
'T Hart et al., Modelling of multiple sclerosis: lessons learned in a non-human primate, Oct. 2004, Lancet Neurol 3:588-597.*
Baker et al., Critical appraisal of animal models of multiple sclerosis, Jun. 2011, Multiple Sclerosis Journal 17(6):647-657.*
Wekerle et al., Animal models of multiple sclerosis, 2006, Drug Discovery Today: Disease Models 3(4):359-367.*
Ransohoff R.M., Animal models of multiple sclerosis: the good, the bad and the bottom line, Aug. 2012, Neuroscience15(8):1074-1077.*
Behan et al., The sad plight of multiple sclerosis research (low on fact, high on fiction): critical data to support it being a neurocristopathy, 2010, Inflammopharmacology 18:265-290.*
Carniglia, Lila, et al.: "Effect of NDP-α-MSH on PPAR-γ and -β Expression and Anti-Inflammatory Cytokine Release in Rat Astrocytes and Microglia," PLOS One, vol. 8(2), pp. 1-11, Feb. 26, 2013.
Catania, Anna: "Neuroprotective Actions of Melanocortins: A Therapeutic Opportunity," Trends in Neuroscience, vol. 31(7), pp. 353-360, Jul. 1, 2008.
Ter Laak, Mariël P., et al.: "The Potent Melanocortin Receptor Agonist Melanotan-II Promotes Peripheral Nerve Regeneration and Has Neuroprotective Properties in the Rat," European Journal of Pharmacology, vol. 462(1-3), pp. 179-183, Feb. 21, 2003.
International Search Report issued in PCT Application No. PCT/EP2014/066816, dated Jan. 5, 2015.
Constantinescu, C. S. et al., Experimental autoimmune encephalomyelitis (EAE) as a model for multiple sclerosis (MS), *British Journal of Pharmacology*, 164:1079-1106, 2011.
Betelli, E. et al., Myelin oligodendrocyte glycoprotein—specific T and B cells cooperate to induce a Devic-like disease in mice, The Journal of Clinical Investigation, 116:23932402, 2006.

* cited by examiner

*Primary Examiner* — John D Ulm
(74) *Attorney, Agent, or Firm* — Seyfarth Shaw LLP

(57) ABSTRACT

The present invention is related to NDP-MSH or pharmaceutically acceptable salts thereof for therapeutic and/or prophylactic therapeutic treatment of inflammatory and/or neurodegenerative disorders of the CNS or multiple sclerosis. The present invention is further related to pharmaceutical compositions and a kit comprising NDP-MSH or pharmaceutically acceptable salts thereof.

18 Claims, 8 Drawing Sheets

Specification includes a Sequence Listing.

• C57BL/6
□ C57BL/6 + NDP-MSH

C57BL/6
+ PBS

C57BL/6
+ NDP-MSH

C57BL/6
+ PBS

C57BL/6
+ NDP-MSH

SEQUENCE LISTING

```
<160> NUMBER OF SEQ ID NOS: 8

<210> SEQ ID NO 1
<211> LENGTH: 13
<212> TYPE: PRT
<213> ORGANISM: Human

<400> SEQUENCE: 1

Ser Tyr Ser Met Glu His Phe Arg Trp Gly Lys Pro Val
1               5                   10

<210> SEQ ID NO 2
<211> LENGTH: 13
<212> TYPE: PRT
<213> ORGANISM: Artificial
<220> FEATURE:
<223> OTHER INFORMATION: NDP-MSH
<220> FEATURE:
<221> NAME/KEY: misc_feature
<222> LOCATION: (4)..(4)
<223> OTHER INFORMATION: X =Norleucine
<220> FEATURE:
<221> NAME/KEY: misc_feature
<222> LOCATION: (7)..(7)
<223> OTHER INFORMATION: X =D-Phenylalanine

<400> SEQUENCE: 2

Ser Tyr Ser Xaa Glu His Xaa Arg Trp Gly Lys Pro Val
1               5                   10
```

```
<210> SEQ ID NO 3
<211> LENGTH: 6
<212> TYPE: PRT
<213> ORGANISM: Artificial
<220> FEATURE:
<223> OTHER INFORMATION: alpha-MSH analogue

<400> SEQUENCE: 3

Glu His Phe Arg Trp Lys
1               5

<210> SEQ ID NO 4
<211> LENGTH: 6
<212> TYPE: PRT
<213> ORGANISM: Artificial
<220> FEATURE:
<223> OTHER INFORMATION: alpha-MSH analogue

<400> SEQUENCE: 4

Asp His Phe Arg Trp Lys
1               5

<210> SEQ ID NO 5
<211> LENGTH: 6
<212> TYPE: PRT
<213> ORGANISM: Artificial
<220> FEATURE:
<223> OTHER INFORMATION: alpha-MSH analogue

<400> SEQUENCE: 5

Arg Trp Lys Gly Pro Val
1               5

<210> SEQ ID NO 6
<211> LENGTH: 4
<212> TYPE: PRT
<213> ORGANISM: Artificial
<220> FEATURE:
<223> OTHER INFORMATION: alpha-MSH analogue

<400> SEQUENCE: 6

Arg Trp Lys Gly
1

<210> SEQ ID NO 7
<211> LENGTH: 5
<212> TYPE: PRT
<213> ORGANISM: Artificial
<220> FEATURE:
<223> OTHER INFORMATION: alpha-MSH analogue

<400> SEQUENCE: 7

Arg Trp Lys Gly Pro
1               5

<210> SEQ ID NO 8
<211> LENGTH: 6
<212> TYPE: PRT
<213> ORGANISM: Artificial
<220> FEATURE:
<223> OTHER INFORMATION: alpha-MSH analogue

<400> SEQUENCE: 8

Arg Trp Lys Gly Pro Val
1               5
```

NDP-MSH FOR TREATMENT OF INFLAMMATORY AND/OR NEURODEGENERATIVE DISORDERS OF THE CENTRAL NERVOUS SYSTEM

This application is a National Stage of PCT/EP2014/066816, filed Aug. 5, 2014, which claims benefit of European Patent Application No. 13 003 909.2, filed Aug. 5, 2013, and European Patent Application No. 13 179 911.6, filed Aug. 9, 2013, the disclosures of which are incorporated herein by reference in their entirety.

FIELD OF THE INVENTION

The present invention is related to NDP-MSH or pharmaceutically acceptable salts thereof for therapeutic and/or prophylactic therapeutic treatment of inflammatory and/or neurodegenerative disorders of the CNS or multiple sclerosis. The present invention is further related to pharmaceutical compositions and a kit comprising NDP-MSH or pharmaceutically acceptable salts thereof.

The instant application contains a Sequence Listing which has been submitted in ASCII format via EFS-Web and is hereby incorporated by reference in its entirety. Said ASCII copy, created on Jul. 6, 2017, is named 14909604_SEQ.txt and is 1.76 kilobytes in size.

BACKGROUND

Disorders of the central nervous system (CNS) are highly prevalent and can affect the brain and/or the spinal cord, resulting in neurological or psychiatric disorders, and occasionally a severe impairment of quality of life. The development of new methods of treatment has addressed a multitude of disorders; but, however, still lags behind other therapeutic areas. This is due to several factors including the complexity of the diseases and the problem of delivering drugs through the blood-brain barrier (BBB). The development of new therapies for CNS disorders could provide patients with significant improvements in quality of life, and reduce the economic burden on health-care systems.

CNS disorders involving inflammation and/or neurodegeneration account for a large proportion of disorders affecting the CNS. They include widely known diseases such as Alzheimer's Disease, Parkinson's Disease and Multiple Sclerosis.

Multiple sclerosis (MS) is a disease of the central nervous system (CNS). It is estimated that number of people affected by MS amounts to 2-2.5 million (approximately 30 per 100,000) worldwide. Pathological manifestations of MS can include multiple inflammatory foci, plaques of demyelination, neuronal injury or loss within the brain or spinal cord, and neuronal dysfunction. MS is typically accompanied by neurological symptoms of variable degrees, including motor, sensory and cognitive deficits, ataxia and visual impairment.

Although the events triggering the onset of MS are still not fully understood, most evidence points toward an autoimmune etiology, possibly together with environmental factors or genetic predisposition. Many elements of the cascade of events leading to MS have been studied in experimental autoimmune encephalomyelitis (EAE), an animal model of autoimmune inflammatory diseases of the CNS which resembles MS in many respects (Constantinescu et al., 2011). Active EAE is induced by immunization of susceptible animals with CNS tissue or myelin peptides, for example myelin basic protein (MBP), proteolipid protein (PLP) or myelin oligodendrocyte glycoprotein (MOG), or their encephalitogenic fragments such as $PLP_{139-151}$ or $MOG_{35-55}$, and appropriate adjuvants. Passive or adoptive-transfer EAE can be induced by transferring pathogenic, myelin-specific T cells to recipient animals. In 2006, Krishnamoorthy et al. further developed transgenic mouse with MOG specific T and B cell receptors that spontaneously develops an inflammatory demyelinating disease resembling Devic's disease, which is often considered a variant of MS.

α-melanocyte-stimulating hormone (α-MSH) is a 13 amino acid peptide derived from a large precursor hormone called pro-opiomelanocortin (POMC). Post-translational cleavage of POMC gives rise to α-MSH in a tissue-specific manner. It has been detected in various regions of the brain and peripheral organs including the skin. Cells producing α-MSH include keratinocytes, melanocytes, Langerhans cells, monocytes, macrophages, endothelial cells, fibroblasts and mast cells. It has been established that α-MSH is not only involved in melanogenesis, but also plays a role in immunity and inflammation (see Luger et al. (2003) for review).

α-MSH exerts its effects through activation of cell-surface bound melanocortin receptors. Five melanocortin receptors (MC-1R to MC-5R) are known. They belong to the G-protein coupled receptors with seven transmembrane domains and are expressed in a cell- and tissue specific manner (see Brzoska et al. for review). The majority of anti-inflammatory effects of α-MSH are associated with to the detection of MC-1R, however, several in vivo studies have linked α-MSH activity to MC-4R (Carniglia et al. 2013).

The anti-inflammatory potential of α-MSH and its role in immunological cascades has been elucidated by several studies. It has been shown to down-regulate the production of pro-inflammatory cytokines (IL-1, IL-6, TNF-α, IL-2, IFN-γ, IL-4, IL-13) and the expression of co-stimulatory molecules (CD86, CD40) and adhesion molecules (ICAM-1, VCAM-1, E-selectin) on antigen-presenting cells. Furthermore, the production of the cytokine synthesis inhibitor IL-10 is up-regulated by α-MSH (Brzoska et al. (2008), Luger et al. (2003)).

The large majority of studies concerned with the investigation of the neuroprotective effect of melanocortins assess the effects of α-MSH, as reviewed in Catania (2008), but fail to recognized the therapeutic potential of NDP-MSH in MS treatment. Brod and Hood (2008) reported that orally administered α-MSH delayed disease onset and decreased disease severity in EAE. Mice were fed with 1, 10 or 100 μg α-MSH starting one week prior to EAE induction by active immunization and continuing through day 14 post immunization. α-MSH prevented or delayed disease onset and was able to reduce the clinical score of affected animals (patented in U.S. Pat. No. 7,807,143). However, the fact that preventive administration of relatively high dosages was necessary on a daily basis renders the approach impracticable for treatment of MS in humans.

Two groups pursued a gene therapy approach in order to deliver sufficient amounts of α-MSH: Yin et al. (2003) generated expression constructs encoding peptides with α-MSH activity and assessed their potential for treatment of EAE in mice. Intramuscular injection of 100 μg of DNA constructs was accomplished concurrently with EAE induction and repeated weekly for a total period of 4 weeks. Treatment with the DNA constructs resulted in delayed disease onset (about 2 days) and a decreased mortality, accounting for the slight reduction of the mean clinical score that was observed.

Han et al. (2008) employed activated transduced T cells specific for the CNS proteolipid (PLP) 139-151 as α-MSH "shuttles". α-MSH producing T cells exhibited an altered cytokine secretion profile and, when transferred to animals with induced or established EAE, could reduce disease incidence delay disease onset. However, although the idea of using auto-reactive T cells as targeted α-MSH shuttles may seem intriguing, the fact that 12.5% of healthy recipient animals developed EAE renders this approach untenable with regard to safety and acceptance as a potential MS therapy.

Therapeutic treatment using α-MSH is hampered because of its inherent instability and short plasma half-life, and its weak receptor interaction (Rudman et al., 1983; Sawyer et al., 1980), resulting in the need of repeated high-dose administration.

However, in 1980 Sawyer et al. succeeded in synthesizing the synthetic α-MSH analog NDP-MSH which exhibited superior biological properties including prolonged biological activity, enhanced potency and resistance to enzymatic degradation (EP0292291). Today, NDP-MSH is marketed as SCENESSE® as a photoprotective drug and has been authorized by the European Medicine's Agency for treatment of erythropoietic protoporphyria. The role of NDP-MSH in inflammatory processes has been assessed, i.e., by Carniglia et al. (2013) who reported that NDP-MSH stimulates the release of IL-10 and TGF-β via MC-4R signaling in rat primary astrocytes and microglia in vitro. The mere observation that rat primary cells—obtained from healthy rat pups—release anti-inflammatory cytokines upon addition of NDP-MSH in vitro can however not suffice to foresee the surprising effects of NDP-MSH on the complex events contributing to disease onset and progression in adult MS model animals. Further, the observations presented herein clearly indicate involvement of MC-1R signaling whereas the effects observed by Carniglia et al. were linked to the detection of MC-4R expression, thereby indicating that the present inventors have revealed a novel mechanism of action of NDP-MSH in inflammatory and/or neurodegenerative processes within the CNS. Ter Laak et al. (2003) discovered that the α-MSH analog melanotan-II is effective in nerve regeneration and neuroprotection, but did not investigate the effect of NDP-MSH, let alone in MS treatment.

There is currently no cure for MS. Therapeutic treatment of MS includes disease-modifying and symptomatic treatments. FDA-approved disease-modifying agents for treatment of relapsing-remitting MS include immunosuppressive agents (mitoxantrone and teriflunomide), immunomodulatory agents such as glatiramer acetate (GA) and the cytokine inhibitor IFN-β, cell-migration modifying therapies including natalizumab and finglomod and neuroprotective agents such as dimethyl-fumarate. While treatment of relapsing-remitting MS is still hampered by adverse side effects or limited clinical efficacy, therapeutic options for secondary progressive MS or primary progressive MS are severely limited (for review see Chen et al. (2012)). There still exists a need in the art to develop alternative drugs for multiple sclerosis treatment.

The technical problem can thus be seen in the provision of an alternative treatment for inflammatory and/or neurodegenerative disorders of the CNS or multiple sclerosis.

SUMMARY

The present inventors have surprisingly discovered that NDP-MSH is able to significantly ameliorate clinical and pathological manifestations in different EAE models, and even prevented recurrence of the disease after the treatment was discontinued. Thus, the present invention provides NDP-MSH or pharmaceutically acceptable salts thereof for use in treatment of multiple sclerosis or inflammatory and/or neurodegenerative disorders of the CNS in a subject. Further, NDP-MSH or pharmaceutically acceptable salts thereof can be used for therapeutic and/or therapeutic prophylactic treatment of inflammatory and neurodegenerative disorders of the CNS or multiple sclerosis in a subject. The subject is preferably a mammal, and in a particularly preferred embodiment the subject is a human.

Preferably, the treatment of inflammatory and/or neurodegenerative disorders of the CNS or MS with NDP-MSH or pharmaceutically acceptable salts thereof thus has an anti-inflammatory and/or neuroprotective effect.

NDP-MSH can be chemically modified, including, e.g., modifications of the C terminus and/or the N-terminus of the peptide. Thus, in some embodiments, treatment of inflammatory and/or neurodegenerative disorders of the CNS or multiple sclerosis in a subject can be accomplished with NDP-MSH or a pharmaceutically acceptable salt thereof that is chemically modified.

Some inflammatory and/or neurodegenerative disorders of the CNS, for example MS, can establish various clinical courses. NDP-MSH or a pharmaceutically acceptable salt thereof can be administered during any phase of the disease, e.g. before onset of the disease, during relapse, remission and/or progression of the disease. It can be administered in any suitable form, however, in one preferred embodiment NDP-MSH or a pharmaceutically acceptable salt thereof is administered intravenously. Alternatively, NDP-MSH or pharmaceutically acceptable salts thereof can be administered as subcutaneous dissolving implants.

A suitable dosage range for NDP-MSH or its pharmaceutically acceptable salt is 0.01 µg-1000 µg/kg of body weight. Preferably, the dosage is about 1-1000 µg/kg, about 1-500 µg/kg or about 1-250 µg/kg of body weight.

For multiple sclerosis treatment or treatment of inflammatory and/or neurodegenerative disorders of the CNS in a patient, NDP-MSH can be administered once, or it can be administered repeatedly, for example in intervals, e.g. every 12 hours, every 24 hours, every 36 hours, every 48 hours, every 60 hours or every 72 hours. In other embodiments, NDP-MSH can be administered every week or every month.

The invention further relates to a pharmaceutical composition comprising NDP-MSH for treatment of inflammatory and/or neurodegenerative disorders of the CNS or multiple sclerosis.

In another aspect, the invention is related to kit for use in the treatment of inflammatory and/or neurodegenerative disorders of the CNS or multiple sclerosis comprising NDP-MSH or pharmaceutically acceptable salts thereof and a carrier. The kit may further comprise one or more agents selected from the group consisting of immunosuppressive agents and anti-inflammatory agents together with a pharmaceutically acceptable carrier or diluent.

DETAILED DESCRIPTION

Figure 1:
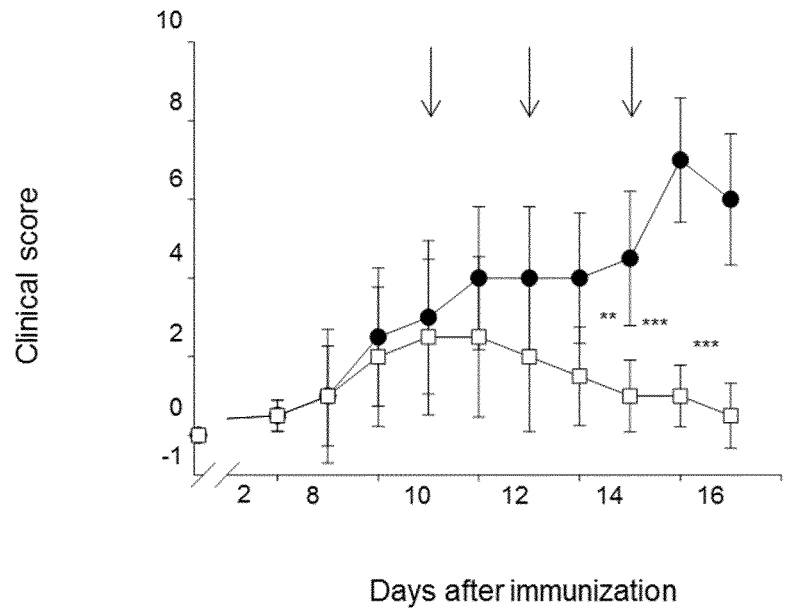
FIG. 1 Effect of systemic NDP-MSH treatment on ongoing Experimental Autoimmune Encephalomyelitis (EAE). C57BL/6 mice were actively immunized by subcutaneous injection of myelin oligodendrocyte glycoprotein ($MOG_{35-55}$) emulsified in Complete Freund's Adjuvant and systemically treated with 5 µg NDP-MSH or PBS every 48 hours beginning at a clinical score of 2-3. Mice were monitored for clinical score (A) and body weight (B) and sacrificed at day 17. Data from n=17 mice in each group is depicted, *, p<0.05 versus PBS-treated controls.
Figure 1:
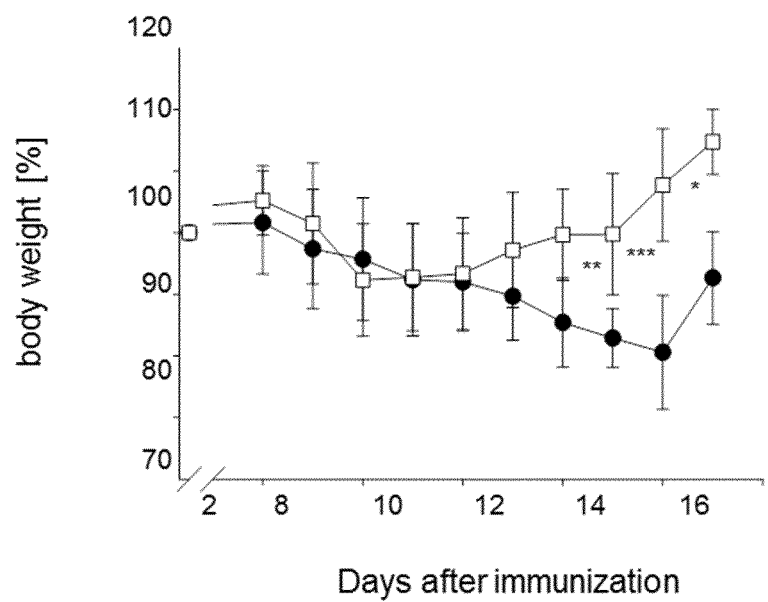
Figure 2:
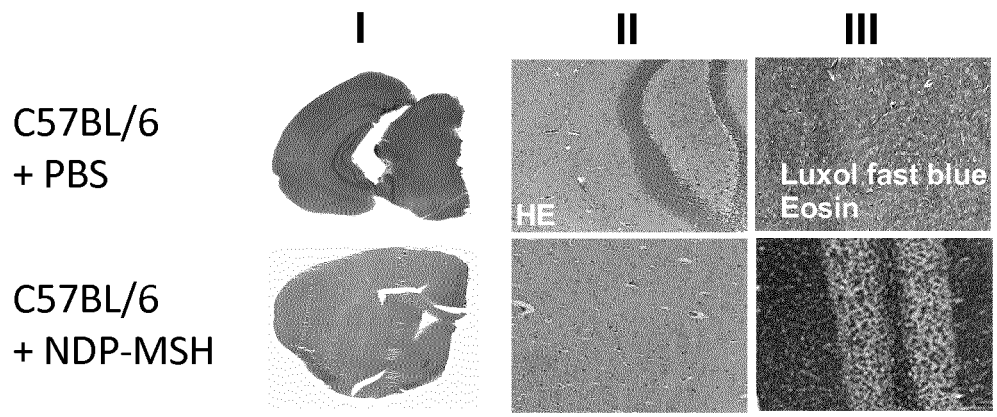
FIG. 2 Histological analyses of brain tissue obtained from mice treated as described in FIG. 1. (A) shows H&E staining of a representative overview (I) and a section enlargement (II) and myelin staining with luxol fast blue (III). (B) shows fluorescence marker staining DAPI/RILP2 (I) and DAPI/APP (II). One representative image for each group (+NDP-MSH, +PBS) is shown.
Figure 2:
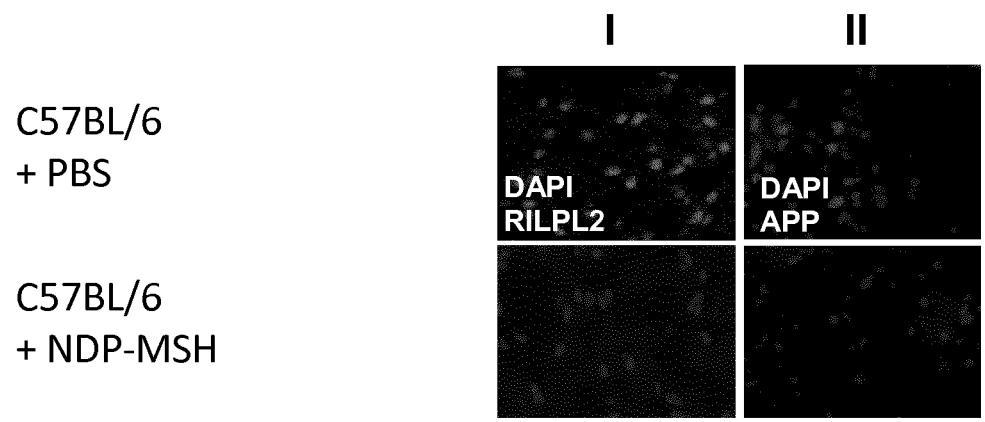
Figure 3:
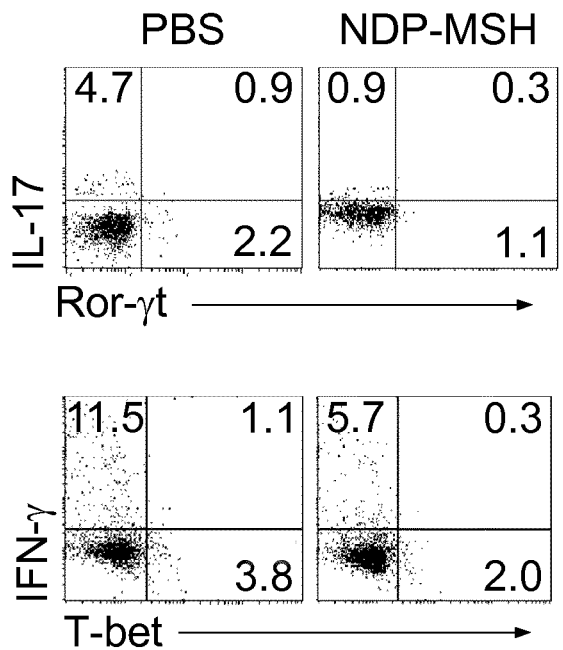
FIG. 3 Effect of NDP-MSH treatment of numbers of pathogenic Th1 and Th17 cells in the CNS. At day 17 post immunization brain and spinal cord from EAE mice treated with PBS and NDP-MSH as described for FIG. 1 were isolated. Cells were analyzed by multi-color flow cytometry using antibodies against CD4, IL-17, ROR-γt, IFN-γ and T-bet. One representative image (A) as well as the statistical evaluation from n=8 mice in each group (B) is shown, Cells are gated for CD4 and IL-17, ROR-γt, IFN-γ as well as T-bet staining was performed after cell permeabilization.
Figure 3:
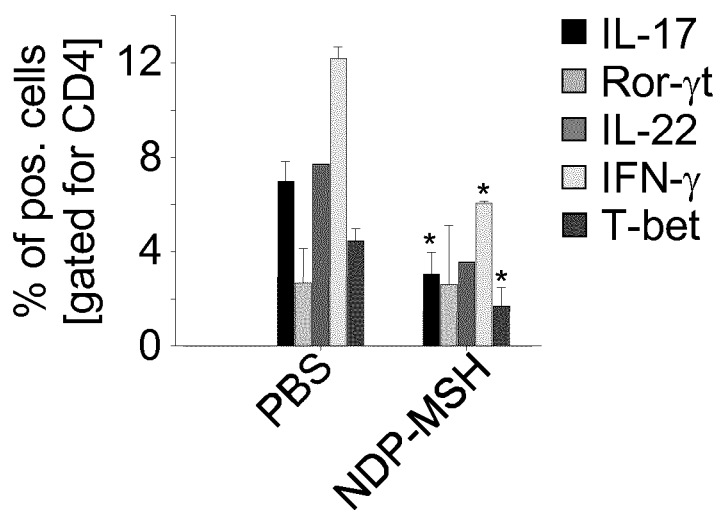
Figure 4:
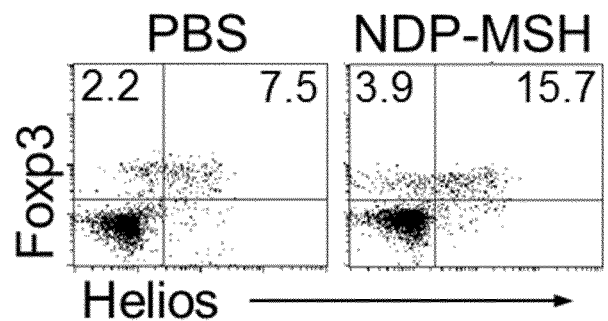
FIG. 4 Induction of functional regulatory T cells in the CNS by NDP-MSH treatment. Numbers, phenotype, and function of Foxp3$^+$ regulatory T cells isolated from brain tissue of NDP-MSH and PBS treated mice were analyzed. One representative dotplot (A) as well as the statistical evaluation from n=6 mice (B) is depicted. Cells are gated for CD4 and Foxp3 as well as Helios staining was performed after cell permeabilization. *, p<0.05 versus PBS treated mice.
Figure 4:
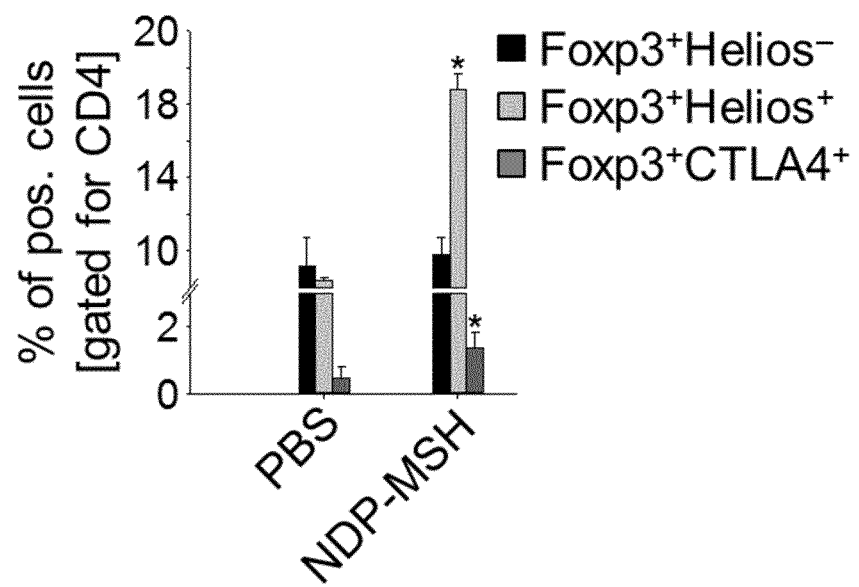
Figure 5:
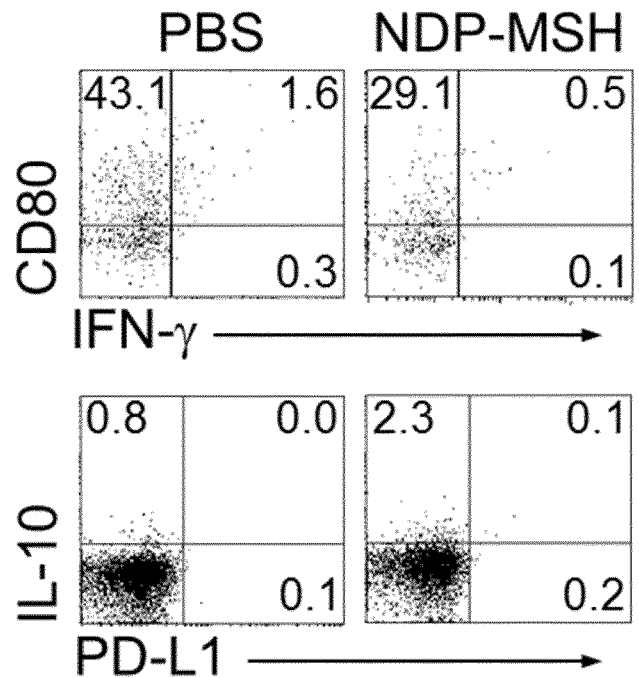
FIG. 5 Generation of tolerogenic dendritic cells by NDP-MSH treatment. The DC phenotype in regional lymph nodes from immunized NDP-MSH and PBS treated mice was analyzed. One representative dot plot (A) as well as the statistical evaluation from n=2-6 mice (B) is depicted. Cells are gated for MHCII and IL-10 as well as IFN-γ staining was performed after cell permeabilization. *, p<0.05 versus PBS treated mice.
Figure 5:
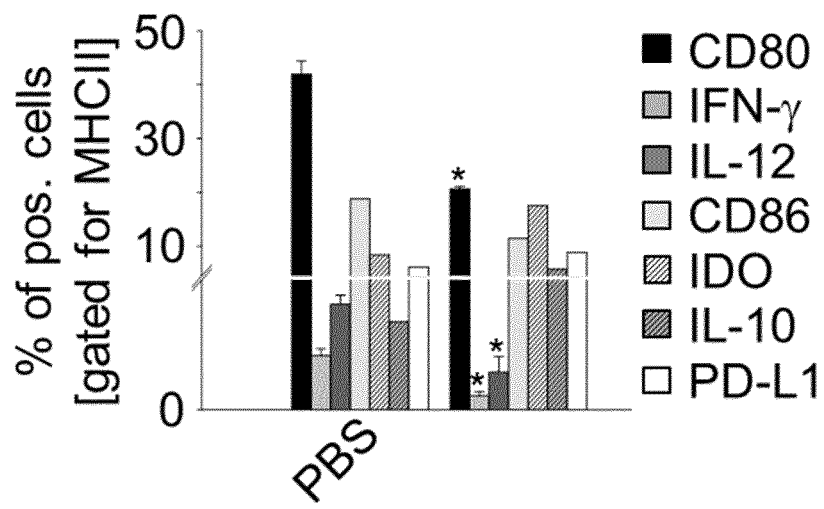
Figure 6:
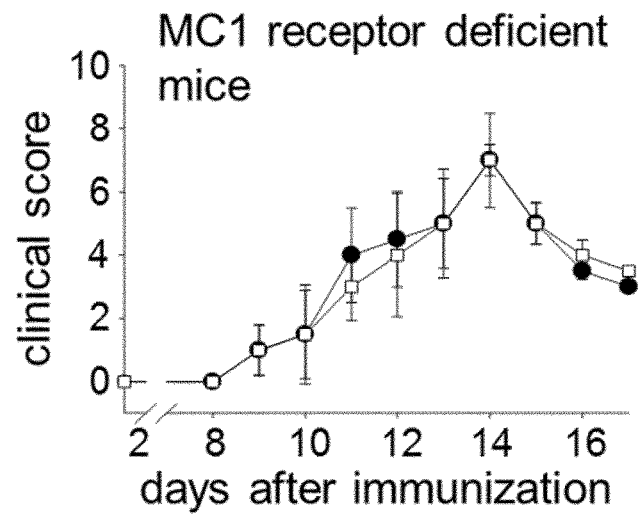
FIG. 6 Involvement of the melanocortin-1 receptor in effects of NDP-MSH on EAE progression. EAE was induced in MC-1R deficient mice as described in FIG. 1. Subsequently, disease development was monitored over time.
Figure 7:
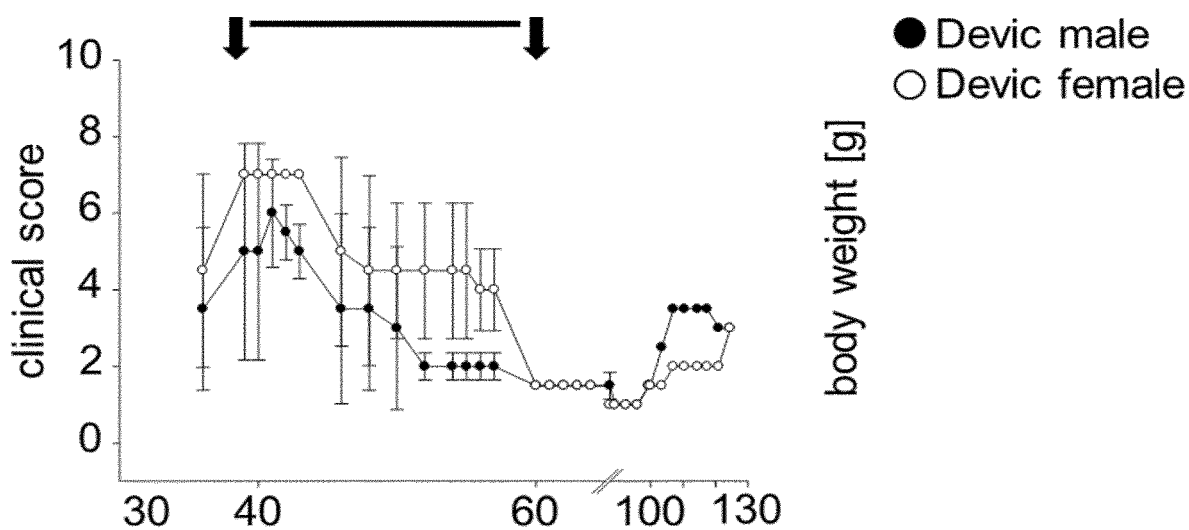
FIG. 7 Devic mice at the age of 38 days and a clinical score of 7 (severe hind limb paralysis) were injected intravenously with 5 µg NDP-MSH every other day for 3 weeks. At day 60, NDP-MSH treatment was interrupted and mice were observed for the onset of clinical symptoms. Disease progression was monitored over time.

To their surprise, the present inventors have discovered that NDP-MSH, a synthetic α-MSH analog that had initially been developed as a potent and stable stimulator of melanogenesis, ameliorates clinical and pathological manifestations in experimental autoimmune encephalomyelitis (EAE) models in mice. Interestingly, NDP-MSH was able to reduce inflammation in the CNS and promote re-myelination of neurons, resulting in attenuation of EAE progression and even complete recovery from EAE symptoms. Notably, even several weeks after NDP-MSH treatment was stopped, no disease recurrence was observed. Thus, NDP-MSH holds considerable potential as a drug for treatment of inflammatory and/or neurodegenerative disorders of the CNS, multiple sclerosis and other inflammatory demyelinating diseases in humans.

The neuropeptide α-MSH is a potent immunomodulator capable of inducing immunosuppression and tolerance. Using the mouse model of experimental autoimmune encephalomyelitis (EAE) the present inventors systemically treated MOG-immunized mice with NDP-MSH before and after the onset of hind limb paralysis. Whereas control mice showed a significant weight loss and developed severe ascending paralysis, mice preemptively injected with NDP-MSH were resistant to EAE development. Notably, therapeutic treatment attenuated EAE progression and prevented mice from weight loss. Flow cytometry, immunofluorescence staining and gene expression analyses revealed the absence of pathogenic Th17 and Th1 cells from brain tissue of NDP-MSH-treated animals. This effect was mediated by up-regulated numbers of Foxp3$^+$ regulatory T cells (Treg) in α-MSH-injected mice versus controls. Since α-MSH has been shown to expand Treg by the induction of tolerogenic dendritic cells (DC) the DC phenotype at different stages of disease was analyzed. DC from NDP-MSH-treated mice expressed increased levels of PD-L1 or IL-10 and down-regulated maturation markers pointing to the induction of a tolerogenic DC phenotype. Since signaling via melanocortin-1-receptor (MC-1R) mediates the immunomodulatory effects of α-MSH, EAE was induced in MC-1R-deficient mice. Interestingly, upon α-MSH injection these mice developed hind limb paralysis similar to PBS treated controls, demonstrating that binding to MC-1R is essential for the NDP-MSH-mediated prevention of EAE. Together, these data indicate that NDP-MSH induces tolerogenic DC and expands functional Treg in vivo. These Treg suppress pathogenic Th1 and Th17 cells during EAE development, suggesting NDP-MSH as a potential therapeutic option for the treatment of patients with moderate multiple sclerosis. Moreover, NDP-MSH was shown to have a strong neuroprotective effect, which was further elucidated by NDP-MSH treatment of EAE in Treg- or DC-depleted mice. Notably, while PBS-treated controls developed severely progressing symptoms from day 10 after immunization, disease development and progression was significantly reduced in NDP-MSH treated animals even in the absence of Treg or DC indicating that NDP-MSH elicits its effects not only by induction of Treg and tolerogenic DC, but also plays a considerable neuroprotective role.

The neuroprotective role of NDP-MSH was further confirmed analyzing neurons from NDP-MSH-treated animals and vehicle-treated controls (isolated before and after MOG immunization) using histological staining tests for the detection of myelin, NeuN, act. Caspase 3 and TUNEL. Further, in vitro stimulation of neurons from embryonic mice with glutamate—which causes cell damage—in the presence or absence of NDP-MSH and subsequent histological staining tests for the detection of myelin, NeuN, act. Caspase 3 and TUNEL indicated that NDP-MSH was able to reduce the glutamate-induced neuronal damage or MOG significantly. Thus, a neuroprotective effect of NDP-MSH is a very likely explanation for the observed effect in the EAE model.

Without wishing to be bound by theory, it is speculated that NDP-MSH exerts its neuroprotective effect by inducing Nur77 expression, a receptor that is normally associated with the T-cell activation. As early as 2008 it was shown that Nur77 can be activated by MC-1R mediated signals and in 2010 Volakakis et al. noted that this receptor, in addition to the activation of T cells, also controls induction of neuroprotective genes in response to oxidative stress (Smith, et al. (2008) Volakilis, et al.(2010)). The present inventors observed an induction of the neuroprotective Nur77 receptor in NDP-MSH stimulated neurons as compared to vehicle-treated controls. To show whether the effect of NDP-MSH on the progression of EAE in vivo was caused by induction of Nur77, Nur77 deficient mouse mutants were subjected to a MOG-induced EAE+/−NDP-MSH treatment. Without wishing to be bound by theory, it is expected that NDP-MSH has no effect on the progression of EAE in Nur77-deficient mice.

"NDP-MSH" also referred to as Afamelanotide or Melanotan-1 or [Nle$^4$, D-Phe$^7$]-α-MSH is a synthetic analog of α-MSH. The term "synthetic analog" is used herein to describe a non-naturally occurring or artificially synthesized compound that is structurally related to a parent compound. "alpha-MSH" or "α-MSH" as used herein means alpha-melanocyte stimulating hormone, a peptide hormone of the melanocortin family. Typically, α-MSH consists of thirteen amino acids having the sequence reflected in SEQ ID NO: 1. Compared to SEQ ID NO: 1, in NDP-MSH, the amino acid corresponding to the amino acid at position 4 is norleucine (abbreviated Nle), and the amino acid corresponding to the amino acid at position 7 is D-phenylalanine (i.e. phenylalanine configurated as D-enantiomer, abbreviated D-Phe). The amino acid sequence of NDP-MSH is shown in SEQ ID NO: 2.

The term NDP-MSH" also includes the alpha-MSH analogues described in U.S. Pat. Nos. 4,457,864; 4,485,039; 4,866,038; 4,918,055; 5,049,547; 5,674,839 and 5,714,576 and Australian Patent Nos. 597630 and 618733 which are herein incorporated by reference for their teachings with respect to alpha-MSH analogues and their synthesis thereof. An alpha-MSH analogue is sometimes also referred to herein as alpha-MSH derivative and, thus, these terms can mutually replace each other.

In one aspect, the alpha-MSH analogue may be a compound as disclosed in AU-Patent No. 597630, selected from compounds of the formula:

R$_1$—W—X—Y—Z—R$_2$ wherein
R$_1$ is absent; n-Pentadecanoyl, Ac, 4-phenylbutyryl; Ac-Gly-, Ac-Met-Glu, Ac-Nle-Glu-, or Ac-Tyr-Glu-;
W is -His- or -D-His-;
X is -Phe-, -D-Phe-, -Tyr-, -D-Tyr-, or -(pNO$_2$)D-Phe$^7$-;
Y is -Arg- or -D-Arg-;
Z is -Trp- or -D-Trp-; and
R$_2$ is —NH$_2$; -Gly-N$_2$; or -Gly-Lys-NH$_2$.

In another aspect, the alpha-MSH analogue may be selected from cyclic analogues which are disclosed in Australian Patent No. 618733 where an intramolecular interaction (such as a disulfide or other covalent bond) exists (1) between the amino acid residue at position 4 and an amino acid residue at position 10 or 11, and/or (2) between the amino acid residue at position 5 and the amino acid residue at position 10 or 11.

The alpha-MSH analogue may be a linear analogue as disclosed in U.S. Pat. No. 5,674,839, selected from the group consisting of:

Ac-Ser-Tyr-Ser-Nle-Glu-His-D-Phe-Arg-Trp-Lys-Gly-Pro-Val-NH$_2$

Ac-Ser-Tyr-Ser-Nle-Asp-His-D-Phe-Arg-Trp-Lys-Gly-Pro-Val-NH$_2$

Ac-Nle-Glu-His-D-Phe-Arg-Trp-Lys-Gly-Pro-Val-NH$_2$

Ac-Nle-Asp-His-D-Phe-Arg-Trp-Lys-Gly-Pro-Val-NH$_2$

Ac-Nle-Asp-His-D-Phe-Arg-Trp-Gly-NH$_2$

Ac-Nle-Glu-His-D-Phe-Arg-Trp-Lys-NH$_2$

Ac-Nle-Asp-His-D-Phe-Arg-Trp-Lys-NH$_2$

Ac-Nle-Glu-His-D-Phe-Arg-Trp-Orn-NH$_2$

Ac-Nle-Glu-His-D-Phe-Arg-Trp-Lys-NH$_2$

Ac-Nle-Asp-His-D-Phe-Arg-Trp-Lys-NH$_2$

Ac-Nle-Glu-His-D-Phe-Arg-Trp-Orn-NH$_2$

Ac-Nle-Asp-His-D-Phe-Arg-Trp-Orn-NH$_2$

Ac-Nle-Glu-His-D-Phe-Arg-Trp-Dab-NH$_2$

Ac-Nle-Asp-His-D-Phe-Arg-Trp-Dab-NH$_2$

Ac-Nle-Glu-His-D-Phe-Arg-Trp-Dpr-NH$_2$

Ac-Nle-Glu-His-L-Phe-Arg-Trp-Lys-NH$_2$

Ac-Nle-Asp-His-L-Phe-Arg-Trp-Lys-NH$_2$

The alpha-MSH analogue may also be a cyclic analogue as disclosed in U.S. Pat. No. 5,674,839, selected from the group consisting of:

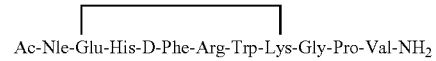
Ac-Nle-Glu-His-D-Phe-Arg-Trp-Lys-Gly-Pro-Val-NH$_2$

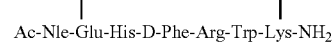
Ac-Nle-Glu-His-D-Phe-Arg-Trp-Lys-NH$_2$

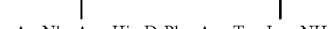
Ac-Nle-Asp-His-D-Phe-Arg-Trp-Lys-NH$_2$

Ac-Nle-Asp-His-D-Phe-Arg-Trp-Orn-NH$_2$

Ac-Nle-Asp-His-D-Phe-Arg-Trp-Dab-NH$_2$

Ac-Nle-Asp-His-D-Phe-Arg-Trp-Dpr-NH$_2$

Ac-Ser-Tyr-Ser-Nle-Asp-His-D-Phe-Arg-Trp-Lys-Gly-Pro-Val-NH$_2$

Ac-Ser-Tyr-Ser-Nle-Asp-His-D-Phe-Arg-Trp-Lys-NH$_2$

-continued

Ac-Tyr-Ser-Nle-Asp-His-D-Phe-Arg-Trp-Lys-NH₂

Ac-Ser-Nle-Asp-His-D-Phe-Arg-Trp-Lys-NH₂

Ac-Nle-Asp-His-D-Phe-Arg-Trp-Lys-NH₂

Ac-Nle-Asp-His-D-Phe-Arg-Trp-Lys-Gly-NH₂

Ac-Nle-Asp-His-D-Phe-Arg-Trp-Lys-Gly-Pro-NH₂

Ac-Nle-Asp-His-D-Phe-Arg-Trp-Lys-Gly-Pro-Val-NH₂

Ac-Ser-Nle-Asp-His-D-Phe-Arg-Trp-Lys-Gly-Pro-Val-NH₂ wherein Ala=alanine, Arg=arginine, Dab=2,4-diaminobutyric acid, Dpr=2,3-diaminopropionic acid, Glu=glutamic acid, Gly=glycine, His=histidine, Lys=lysine, Met=methionine, Nle=norleucine, Orn=ornithine, Phe=phenylalanine, (pNO₂)Phe=paranitrophenylalanine, Plg=phenylglycine, Pro=proline, Ser=serine, Trp=tryptophan, TrpFor=N¹⁻formyl-tryptophan, Tyr=tyrosine, Val=valine.

All peptides are written with the acyl-terminal end at the left and the amino terminal end to the right; the prefix "D" before an amino acid designates the D-isomer configuration, and unless specifically designated otherwise, all amino acids are in the L-isomer configuration.

In one aspect of the present invention, the alpha-MSH analogue can be

[D-Phe⁷]-alpha-MSH,

[Nle⁴, D-Phe⁷]-alpha-MSH,

[D-Ser¹, D-Phe⁷]-alpha-MSH,

[D-Tyr², D-Phe⁷]-alpha-MSH,

[D-Ser³, D-Phe⁷]-alpha-MSH,

[D-Met⁴, D-Phe⁷]-alpha-MSH,

[D-Glu⁵, D-Phe⁷]-alpha-MSH,

[D-His⁶, D-Phe⁷]-alpha-MSH,

[D-Phe⁷, D-Arg⁸]-alpha-MSH,

[D-Phe⁷, D-Trp⁹]-alpha-MSH,

[D-Phe⁷, D-Lys¹¹]-alpha-MSH,

[D-Phe-⁷, D-Pro¹²]-alpha-MSH,

[D-Phe⁷, D-Val¹³]-alpha-MSH,

[D-Ser¹, Nle⁴, D-Phe⁷]-alpha-MSH,

[D-Tyr², Nle⁴, D-Phe⁷]-alpha-MSH,

[D-Ser³, Nle⁴, D-Phe⁷]-alpha-MSH,

[Nle⁴, D-Glu⁵, D-Phe⁷]-alpha-MSH,

[Nle⁴, D-His⁶, D-Phe⁷]-alpha-MSH,

[Nle⁴, D-Phe⁷, D-Arg⁸]-alpha-MSH,

[Nle⁴, D-Phe⁷, D-Trp⁹]-alpha-MSH,

[Nle⁴, D-Phe⁷, D-Lys¹¹]-alpha-MSH,

[Nle⁴, D-Phe⁷, D-Pro¹²]-alpha-MSH,

[Nle⁴, D-Phe⁷, D-Val¹³]-alpha-MSH,

[Cys⁴, Cys¹⁰]-alpha-MSH

[Cys⁴, D-Phe⁷, Cys¹⁰]-alpha-MSH

[Cys⁴, Cys¹¹]-alpha-MSH

[Cys⁵, Cys¹⁰]-alpha-MSH

[Cys⁵, Cys¹¹]-alpha-MSH

[Cys⁴, Cys¹⁰]-alpha-MSH₄₋₁₃

[Cys⁴, Cys¹⁰]-alpha-MSH₄₋₁₂

[Nle⁴, D-Phe⁷]-alpha-MSH₄₋₁₀,
[Nle⁴, D-Phe⁷]-alpha-MSH₄₋₁₁,
[D-Phe⁷]-alpha-MSH₅₋₁₁,
[Nle⁴, D-Tyr⁷]-alpha-MSH₄₋₁₁,
[(pNO₂)D-Phe⁷]-alpha-MSH₄₋₁₁,
[Tyr⁴, D-Phe⁷]-alpha-MSH₄₋₁₀,
[Tyr⁴, D-Phe⁷]-alpha-MSH₄₋₁₁,
[Nle⁴]-alpha-MSH₄₋₁₁,
[Nle⁴, (pNO₂)D-Phe⁷]-alpha-MSH₄₋₁₁,
[Nle⁴, D-His⁶]-alpha-MSH₄₋₁₁,
[Nle⁴, D-His⁶, D-Phe⁷]-alpha-MSH₄₋₁₁,
[Nle⁴, D-Arg⁸]-alpha-MSH₄₋₁₁,
[Nle⁴, D-Trp⁹]-alpha-MSH₄₋₁₁,
[Nle⁴, D-Phe⁷, D-Trp⁹]alpha-MSH₄₋₁₁,
[Nle⁴, D-Phe⁷]-alpha-MSH₄₋₉, or
[Nle⁴, D-Phe⁷, D-Trp⁹]-alpha-MSH₄₋₉.

In a further aspect, the alpha-MSH analogue is:
[Nle⁴, D-Phe⁷]-alpha-MSH₄₋₁₀,
[Nle⁴, D-Phe⁷]-alpha-MSH₄₋₁₁,
[Nle⁴, D-Phe⁷, D-Trp⁹]-alpha-MSH₄₋₁₁, or
[Nle⁴, D-Phe⁷]-alpha-MSH₄₋₉.

In a particularly preferred aspect, the alpha-MSH analogue is [Nle⁴, D-Phe⁷]-alpha-MSH.

For the purpose of the invention the active compound as defined above also includes the pharmaceutically acceptable salt(s) thereof. The phrase "pharmaceutically or cosmetically acceptable salt(s)", as used herein, means those salts of compounds of the invention that are safe and effective for the desired administration form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The use of salt formation as a means of varying the properties of pharmaceutical compounds is well known and well documented. Salt formation can be used to increase or decrease solubility, to improve stability or toxicity and to reduce hygroscopicity of a drug product. There are a wide range of chemically diverse acids and bases, with a range of pKa values, molecular weights, solubilities and other properties, used for this purpose. Of course, any counterions used in pharmaceuticals must be considered safe, and several lists of pharmaceutically approved counterions exist, which vary depending on the source. Approved salt formers can e.g. be found in the Handbook of Pharmaceutical Salts (Stahl P H, Wermuth C G, editors. 2002. Handbook of pharmaceutical salts: Properties, selection and use. Weinheim/Zurich:

Wiley-VCH/VHCA.). Thus, the present invention also comprises the use of pharmaceutically acceptable salts of NDP-MSH for the treatment of inflammatory and/or neurodegenerative disorders of the CNS or multiple sclerosis.

"Inflammatory and/or neurodegenerative disorders of the CNS" are disorders associated with inflammation and/or neurodegeneration that affect the CNS. However, some disorders may also affect the peripheral nervous system (PNS). "Inflammatory and/or neurodegenerative disorders" means that some of the disorders are associated with neurodegeneration in the CNS, while others are associated with inflammation in the CNS, and some are associated with both neurodegeneration and inflammation in the CNS. Inflammatory and/or neurodegenerative disorders of the CNS include, but are not limited to, Alzheimer's disease, Amyotrophic lateral sclerosis (ALS), Friedreich's ataxia, Huntington's disease, Lewy body disease, Parkinson's disease, Spinal muscular atrophy (SMA), Spinocerebellar ataxia (SCA), Multiple Sclerosis (MS), Marburg variant of MS, Baló's concentric sclerosis, Schilder's disease, acute disseminated encephalomyelitis (ADEM), and Devic's disease, also referred to as neuromyelitis optica (NMO), Optic-spinal MS, Acute hemorrhagic leukoencephalitis, Solitary sclerosis, Optic neuritis, Transverse myelitis. It is to be understood that treatment of any other disorder involving inflammation and/or neurodegeneration in the CNS is also envisaged.

"Multiple sclerosis" or "MS", also sometimes referred to as disseminated sclerosis or encephalomyelitis disseminata, is a disease that affects the central nervous system (CNS). The CNS is a part of the nervous system comprising the brain and the spinal cord. MS can be associated with a wide range of neurological symptoms, including paralysis, sensory and cognitive defects, spasticity, tremor, lack of coordination and visual impairment.

Typically, MS is categorized in the following subtypes: a) relapsing-remitting MS (RRMS), which affects about 85% of MS patients and is characterized by relapses (acute attacks) of disease followed by periods of partial or full recovery (remission); b) secondary progressive MS (SPMS) which begins with an initial relapsing-remitting disease course, followed by ongoing disease progression that may include occasional relapses and minor remissions and plateaus, i.e. periods without a change in health condition, c) primary progressive MS (PPMS), which affects approximately 10% of MS patients and is characterized by disease progression from the onset, most frequently in the absence of relapses, and d) progressive-relapsing MS, which is the least common disease course showing disease progression from onset but with clear acute relapses.

It is envisaged that NDP-MSH can be used for treatment of MS in any of the forms and/or phases described herein. For example, NDP-MSH can be used for treatment of relapsing-remitting MS during relapse and/or during remission. It is further envisaged that NDP-MSH can be used for prophylactic therapeutic treatment of subjects that are at risk of developing MS or another inflammatory and/or neurodegenerative disease, for example individuals that have developed clinically isolated syndrome (CIS), the first clinical episode of symptoms and signs suggestive of an inflammatory demyelinating disorder of the central nervous system.

Preferably, NDP-MSH treatment results in amelioration and/or remission of clinical and/or pathological manifestations and/or symptoms associated with MS or the inflammatory and/or neurodegenerative disorder.

Typical pathological manifestations of MS or inflammatory and/or neurodegenerative disorders include, but are not limited to, inflammation, de-myelination and neurodegeneration in the CNS. Thus, treatment with NDP-MSH preferably results in an anti-inflammatory and/or neuroprotective effect.

Without wishing to be bound by a specific theory, it is thought that MS is triggered by CNS-autoreactive T cells that become activated in the periphery and differentiate into Th1 (producing, e.g., IFN-γ) or Th17 cells (producing, e.g., IL-17, IL-22, IL-21). Activated T-cells can up-regulate integrins such as VLA-4 and cross the blood brain barrier (BBB), the interface that separates the brain from the circulatory system and protects the CNS. On encountering their cognate antigen in the CNS, the T cells proliferate and secrete pro-inflammatory cytokines which in turn stimulate microglia, macrophages and astrocytes, and recruit B cells, ultimately resulting in demyelination and axonal loss.

Having an "anti-inflammatory" effect in general means controlling and/or reducing any step of the inflammation cascade triggering and/or contributing to MS pathology or pathology of the inflammatory and/or neurodegenerative disorder. The person skilled in the art readily knows how to assess the anti-inflammatory effect of NDP-MSH, e.g. by measuring the expression of certain marker proteins associated with CNS inflammation, such as, e.g., Rab-interacting lysosomal protein (RILP) 2. This can, for example, be accomplished by immunofluorescence staining with antibodies recognizing the marker protein and linked to (labeled with) a fluorophore. Other methods include monitoring populations of pro-inflammatory cells in the CNS that are associated with disease onset and/or progression. For example, in MS, Th1 and Th17 cell populations are thought to be involved in inflammatory processes in the CNS contributing to disease onset/progression. The person skilled in the art knows how to assess specific cell populations, e.g., by fluorescence-activated cell sorting (FACS). The method has been extensively described in the prior art. Another method to survey inflammatory processes is to assess levels of pro-inflammatory cytokines, e.g. by ELISA (enzyme-linked immunosorbent assay).

Having a "neuroprotective" effect as used herein means having the effect of preventing neurodegeneration. "Neurodegeneration" is used herein to describe neuronal and/or axonal injury and/or loss. The events leading to neurodegeneration have not fully been elucidated, however, without wishing to be bound by a specific theory, it is presumed that in some inflammatory and/or neurodegenerative disorders of the CNS or MS, inflammation and/or de-myelination may be involved. "Demyelination" means damage and/or loss of the myelin sheath. Myelin is composed of water, lipids and proteins and is typically deposited in layers around axons. The myelin sheath functions as an electrical insulation and thereby increases the speed of impulses propagating along the myelinated axons. When myelin is damaged or degenerated, conduction of signals along the nerve can be impaired or lost. It is assumed that loss of the myelin sheath may result in neurodegeneration. Demyelination can, for example, be visualized with a suitable dye, such as, e.g. luxol, in a sample. Further, magnetic resonance imaging (MRI) can be used for visualizing plaques of demyelination in the brain.

NDP-MSH or pharmaceutically acceptable salts thereof used according to the invention may be chemically modified. Generally, all kind of modifications of NDP-MSH or pharmaceutically acceptable salts thereof are comprised by the present invention as long as they do not inhibit the therapeutic effect of the peptide or salt respectively. E.g. modifications at the N terminus and/or at the C terminus of the peptide might be performed, for example by an acyl group, preferably an acetyl group at the N terminus and/or an amidation or esterification of the C terminus.

Other chemical modifications of the compounds of the invention such as alkylation (e.g., methylation, propylation, butylation), arylation, etherification and esterification may be possible and are also envisaged. It is preferred that the mentioned modifications do not significantly alter the advantageous capabilities of the compounds of the invention as described herein, i.e. the chemically modified compounds of the invention have capabilities which are comparable with the capabilities of the compounds which were evaluated in the appended examples. "Comparable" is explained herein below.

It may be necessary, for reasons of resistance to degradation, to employ a protected form of the compounds of the invention. The nature of the protecting group must obviously be a biologically compatible form. Many biologically compatible protective groups are suitable, such as, for example, those provided by acylation or acetylation of the amino-terminal end or amidation of the carboxy-terminal end.

Thus, the invention also features the compounds of the invention in a protected or unprotected form. Protective groups based either on acylation or acetylation of the amino-terminal end or on amidation of the carboxy-terminal end or, alternatively, on both, are the preferred.

Further protective groups known per se are likewise possible. The modifications may also affect the amino group in the side chains of the amino acids. As stated above, it is preferred that these modifications do not significantly alter the advantageous capabilities of the compounds of the invention as described herein.

In a more preferred embodiment of the invention the above mentioned tripeptides are amidated at the C-terminus.

Thus, a further embodiment of the present invention is the use of the NDP-MSH or pharmaceutically acceptable salts thereof which are chemically modified.

In the context with the present invention the term "treatment" and all its grammatical forms thereof includes therapeutic or prophylactic treatment. A "therapeutic or prophylactic treatment" comprises prophylactic treatments such as complete prevention of occurrence of symptoms or therapeutic treatment for improvement or amelioration of already occurred symptoms or in order to prevent further aggravation of disease (activity). As for effectiveness of the prophylactic and/therapeutic treatment, the term should be construed in its broadest sense including improvement of findings diagnosed by a doctor and improvement of rational symptoms.

NDP-MSH or a pharmaceutically acceptable salt thereof as described above is preferably applied in the treatment of mammals, particularly of humans.

According to one embodiment of the present invention the inventive use of NDP-MSH or a pharmaceutically acceptable salt thereof leads to a direct or indirect interaction with the melanocortin receptor 1 (MC-R1).

NDP-MSH or the pharmaceutically acceptable salts thereof might also be used as part of a composition. Thus, a further embodiment of the invention is the use of NDP-MSH or pharmaceutically acceptable salts thereof for the manufacture of a pharmaceutical composition for treatment of multiple sclerosis or inflammatory and/or neurodegenerative disorders of the CNS. NDP-MSH or the pharmaceutically acceptable salts thereof can also be used to produce a medicament for the treatment and/or prevention of multiple sclerosis or inflammatory and/or neurodegenerative disorders of the CNS. The embodiments indicated above are encompassed analogously by this use. NDP-MSH or the pharmaceutically acceptable salts thereof are normally mixed with a pharmaceutically acceptable carrier or diluent. Processes known per se for producing medicaments are indicated in Forth, Henschler, Rummel (1996) Allgemeine und spezielle Pharmakologie und Toxikologie, Urban & Fischer.

Pharmaceutical compositions of the invention comprise a therapeutically effective amount of the compound of the present invention or a pharmaceutically acceptable salt thereof and can be formulated in various forms, e.g. in solid, liquid, powder, aqueous, lyophilized form. The pharmaceutical composition may be administered with a pharmaceutically acceptable carrier to a patient, as described herein. In a specific embodiment, the term "pharmaceutically acceptable" means approved by a regulatory agency or other generally recognized pharmacopoeia for use in animals, and more particularly in humans. Accordingly, the pharmaceutical composition may further comprise a pharmaceutically acceptable carrier or excipient. Pharmaceutically acceptable carriers, which may be used in formulating the composition according the invention, comprise those described below for the composition. Other suitable pharmaceutically acceptable carriers and excipients are inter alia described in Remington's Pharmaceutical Sciences, 15$^{th}$ Ed., Mack Publishing Co., New Jersey (1991) and Bauer at al, Pharmazeutische Technologie, 5$^{th}$ Ed., Govi-Verlag Frankfurt (1997).

It is also envisaged that the pharmaceutical composition may optionally further comprise one or more of the group selected from immunosuppressive agents and anti-inflammatory agents. The person skilled in the art knows how to select suitable agents for treatment of the specific inflammatory and/or neurodegenerative disorder of the CNS or MS. Exemplary suitable agents include, but are not limited to, corticosteroids.

The present invention relates also to a kit for the treatment of inflammatory and/or neurodegenerative disorders of the CNS or multiple sclerosis comprising NDP-MSH or pharmaceutically acceptable salt thereof and a carrier. It is also envisaged that the kit may optionally further comprise one or more of the group selected from immunosuppressive agents and anti-inflammatory agents. The person skilled in the art knows how to select suitable agents for treatment of the specific inflammatory and/or neurodegenerative disorder of the CNS or MS. Exemplary suitable agents include, but are not limited to, corticosteroids.

Generally all carriers are suitable that are pharmaceutically acceptable. Generally all types of carriers are suitable for the use according to the present invention that enable a release at the desired sit of action. The person skilled in the art knows which type of carrier is suitable depending on the correspondent application form.

Carriers might be biodegrade such as Liposomes; Microspheres made of the biodegradable polymer poly(lactic-co-glycolic) acid, albumin microspheres; synthetic polymers (soluble); nanofibers, protein-DNA complexes; protein conjugates; erythrocytes virosomes. Various carrier based dosage forms comprise solid lipid nanoparticles (SLNs), polymeric nanoparticles, ceramic nanoparticles, hydrogel nanoparticles, copolymerized peptide nanoparticles, nanocrystals and nanosuspensions, nanocrystals, nanotubes and nanowires, functionalized nanocarriers, nanospheres, nanocapsules, liposomes, lipid emulsions, lipid microtubules/microcylinders, lipid microbubbles, lipospheres, lipopolyplexes, ethosomes, multicomposite ultrathin capsules, aquasomes, pharmacosomes, colloidosomes, niosomes, discomes, proniosomes, microspheres, microemulsions and polymeric micelles.

Polymers are the backbone of the typical transdermal drug delivery systems. Systems for transdermal delivery are fabricated as multi-layered polymeric laminates in which a drug reservoir or a drug-polymer matrix is sandwiched between two polymeric layers: an outer impervious backing layer that prevents the loss of drug through the backing surface and an inner polymeric layer that functions as an adhesive and/or rate-controlling membrane. Transdermal drug delivery systems comprise different systems such as the reservoir systems, microreservoir systems, and the combination of reservoir and matrix-dispersion systems.

In the reservoir system, the drug reservoir is embedded between an impervious backing layer and a rate-controlling membrane. The drug releases only through the rate-controlling membrane, which can be microporous or non-porous. In the drug reservoir compartment, the drug can be in the form of a solution, suspension, or gel or dispersed in a solid polymer matrix. On the outer surface of the polymeric membrane a thin layer of drug-compatible, hypoallergenic adhesive polymer can be applied. In the Matrix systems and Drug-in-adhesive system the drug reservoir is formed by dispersing the drug in an adhesive polymer and then spreading the medicated polymer adhesive by solvent casting or by melting the adhesive (in the case of hot-melt adhesives) onto an impervious backing layer. On top of the reservoir, layers of unmedicated adhesive polymer are applied. In the Matrix-dispersion system the drug is dispersed homogeneously in a hydrophilic or lipophilic polymer matrix. This drug-containing polymer disk then is fixed onto an occlusive baseplate in a compartment fabricated from a drug-impermeable backing layer. Instead of applying the adhesive on the face of the drug reservoir, it is spread along the circumference to form a strip of adhesive rim. The drug delivery system is a combination of reservoir and matrix-dispersion systems. The drug reservoir is formed by first suspending the drug in an aqueous solution of water-soluble polymer and then dispersing the solution homogeneously in a lipophilic polymer to form thousands of unleachable, microscopic spheres of drug reservoirs. The thermodynamically unstable dispersion is stabilized quickly by immediately cross-linking the polymer in situ. Transdermal drug delivery technology represents one of the most rapidly advancing areas of novel drug delivery. This growth is catalyzed by developments in the field of polymer science. This article focuses on the polymeric materials used in transdermal delivery systems, with emphasis on the materials' physicochemical and mechanical properties, and it seeks to guide formulators in the selection of polymers. Polymers are used in transdermal delivery systems in various ways, including as matrix formers, rate-controlling membranes, pressure-sensitive adhesives (PSAs), backing layers or release liners.

Polymers used in transdermal delivery systems should have biocompatibility and chemical compatibility with the drug and other components of the system such as penetration enhancers and PSAs. They also should provide consistent, effective delivery of a drug throughout the product's intended shelf life or delivery period and have generally-recognized-as-safe status.

Depending on the correspondent need the skilled person will choose the suitable carrier in order to apply NDP-MSH or pharmaceutically acceptable salt according to the present invention. E.g. carriers in the context with e.g. a rectal application are e.g. multi matrix systems using methacrylic acid copolymers.

If e.g. the desired site of action is the colon and NDP-MSH or a pharmaceutically acceptable salt thereof is applied orally the carrier has to be resistant to gastric acid in order to enable a release of NDP-MSH or the pharmaceutically acceptable salt thereof in the colon.

The administration of or the pharmaceutical composition comprising NDP-MSH or pharmaceutically acceptable salts thereof can be done in a variety of ways, including, but not limited to, topically, transdermally, subcutaneously, intravenously, intraperitoneally, intramuscularly or intraocularly. Subcutaneous administration can be accomplished by providing a subcutaneous implant comprising a suitable amount of NDP-MSH or the pharmaceutically acceptable salt thereof, for example about 16-20 mg. However, any other NDP-MSH dosage may be applied if necessary. In one preferred embodiment, NDP-MSH or pharmaceutically acceptable salts thereof or the pharmaceutical composition according to the present invention is administered intravenously.

The exact dose will depend on the purpose of the treatment (e.g. remission maintenance vs. acute flare of disease), and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art. A typical dose can be, for example, in the range of 0.01 to 1000 µg/kg body weight; however, doses below or above this exemplary range are envisioned, especially considering the aforementioned factors.

A suitable dose for administration lies e.g. in the range of 0.1-1000 µg/kg, for example about 1-1000 µg/kg, about 1-500 µg/kg, or about 1-250 µg/kg of body weight.

NDP-MSH can be administered once, or it can be administered repeatedly, for example in intervals, e.g. every 12 hours, every 24 hours, every 36 hours, every 48 hours, every 60 hours or every 72 hours. In other embodiments, NDP-MSH can be administered every week or every month.

The pharmaceutical composition according to the invention may be in solid, liquid or gaseous form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for the desired method of administration, in particular systemic administration.

Rectal applications can be compounded in many forms. Liquid rectal medicine solutions are given by enema. Creams, lotions and ointments are applied externally or inserted internally using an applicator. Suppositories might be prepared by mixing medicine with a wax-like substance to form a semi-solid, bullet-shaped form that will melt after insertion into the rectum. Intraperitoneal injection or IP injection is the injection of a substance into the peritoneum (body cavity). In humans, the method is used to administer chemotherapy drugs to treat some cancers. A further form of administration of an inventive composition is the topic administration, for instance in form of an ointment or cream. Such an ointment or cream may additionally comprise conventional ingredients, like carriers or excipients as described above.

NDP-MSH or the pharmaceutically acceptable salts thereof can also be used in sprays, for example for inhalation. NDP-MSH or the pharmaceutically acceptable salts thereof may also be added to foods.

The present invention is also related to a kit for treatment of inflammatory and/or neurodegenerative disorders of the CNS or multiple sclerosis comprising NDP-MSH or pharmaceutically acceptable salts thereof and a carrier. The inventive kit might be a kit of two or more parts and might be prepared for use in order to apply the kit in in order to treat inflammatory and/or neurodegenerative disorders of the CNS or multiple sclerosis.

It is to be understood that all embodiments, definition, etc. disclosed in the context of treatment are fully applicable to methods of treatment as well. The present invention relates to a method of treatment of inflammatory and/or neurodegenerative disorders of the CNS or multiple sclerosis in a subject in need thereof, comprising administering a pharmaceutically effective amount of NDP-MSH or a pharmaceutically acceptable salt thereof. By "therapeutically effective amount" or "therapeutically active" is meant a dose of a NDP-MSH or a pharmaceutically acceptable salt thereof that produces the therapeutic effects for which it is administered. The exact dose will depend on the purpose of the treatment, and will be ascertainable by one skilled in the art using known techniques. As is known in the art and described above, adjustments for age, body weight, general health, sex, diet, drug interaction and the severity of the condition may be necessary, and will be ascertainable with routine experimentation by those skilled in the art. The therapeutic effect of the respective methods or method steps of the present invention is additionally detectable by all established methods and approaches which will indicate a therapeutic effect. It is, for example, envisaged that the therapeutic effect is detected by way of an improvement or amelioration of the neurological symptoms known in the art for inflammatory and/or neurodegenerative disorders of the CNS or multiple sclerosis, e.g., those described herein. Additionally or alternatively it is also possible to evaluate the general appearance of the respective patient (e.g., fitness, well-being) which will also aid the skilled practitioner to evaluate whether a therapeutic effect is already there. The skilled person is aware of numerous other ways which will enable him or her to observe a therapeutic effect of the compounds of the present invention.

A better understanding of the present invention and of its advantages will be had from the following examples, offered for illustrative purposes only. The examples are not intended to limit the scope of the present invention in any way.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

CITED LITERATURE

Brod, S. A., & Hood, Z. M. (2008). Ingested (oral) alpha-MSH inhibits acute EAE. *Journal of Neuroimmunology,* 193, pp. 106-112.

Brzoska, T., Luger, T. A., Maaser, C., Abels, C., & Bohm, M. (2007). alpha-Melanocyte Stimulating Hormone and Related Tripeptides: Biochemistry, Antiinflammatory and Protective Effects in Vitro and in Vivo, and Future Perspectives for the Treatment of Immune-mediated Inflammatory Diseases. *Endocrine Reviews,* 29(5), pp. 581-602.

Carniglia, L., Durand, D., & Lasaga, M. (2013). Effect of NDP-alpha-MSH on PPAR-gamma and -beta Expression and Anti-Inflammatory Cytokine Release in Rat Astrocytes and Microglia. *PLoS ONE,* 8(2).

Catania, A. (2008). Neuroprotective actions of melanocortins: a therapeutic opportunity. *Trends Neurosci.,* 31(7), pp. 353-360.

Chen, S.-J., Wang, Y.-L., Fan, H.-C., Lo, W.-T., Wang, C.-C., & Sytwu, H.-K. (2012). Current Status of Immunomodulation and Immunimediated Therapeutic Strategies for Multiple Sclerosis. *Clinical and Developmental Immunology.*

Constantinescu, C. S., Farooqi, N., O'Brien, K., & Gran, B. (2011). Experimental autoimmune ecephalomyelitis (EAE) as a model for multiple sclerosis (MS). *British Journal of Pharmacology,* 164, pp. 1079-1106.

Han, D., Tian, Y., Zhang, M., Zhou, Z., & Lu, J. (2007). Prevention and treatment of experimental autoimmune encephalomyelitis with recombinant adeno-associated virus-mediated alpha-melanocyte stimulating hormone-transduced PLP-139-151-specific T cell. *Gene Therapy,* 14, pp. 383-395.

Hochweller, K., Striegler, J., Hammerling, G. J., & Garbi, N. (2008). A novel CD11c.DTR transgenic mouse for depletion of dendritic cells reveals their requirement for homeostatic proliferation of natural killer cells. *European Journal of Immunology,* 38(10), pp. 2776-83.

Krishnamoorthy, G., Lassmann, H., Wekerle, H., & Holz, A. (2006). Spontaneous opticospinal encephalomyelitis in a double-transgenic mouse model of autoimmune T cell/B cell cooperation. *The Journal of Clinical Investigation,* 116(9), pp. 2385-2392.

Kurtzke, J. F. (1983). Rating neurologic impairment in multiple sclerosis: an expanded disability status scale (EDSS). *Neurology,* 33(11), pp. 1444-1452.

Lahl, K., Loddenkemper, C., Drouin, C., Freyer, J., Arnason, J., Eberl, G., . . . Sparwasser, T. (2007). Selective depletion of Foxp3+ regulatory T cells induces a scurfy-like disease. *The Journal of Experimental Medicine,* 204(1), pp. 57-63.

Luger, T. A., Scholzen, T. E., Brzoska, T., & Bohm, M. (2003). New Insights into the Fuctions alpha-MSH and Related Peptides in the Immune System. *Annals New York Academy of Sciences,* pp. 133-140.

Rudman, D., Hollins, B. M., Kutner, M. H., Moffitt, S. D., & Lynn, M. J. (1983). Three types of alpha-melanocyte-stimulating hormone: bioactivities and half-lives. *American Journal of Physiology,* 245(1), pp. E47-54.

Sawyer, T. K., Sanfilippo, P., Hruby, V. J., Engel, M. H., Heward, C. B., Burnett, J., & Hadley, M. E. (1980). 4-Norleucine, 7-D-phenylalanine-alpha-melanocyte-stimulating hormone: A highly potent alpha-melanotropin with ultralong biological activity. (5758, Ed.) *Proceedings of the National Academy of Sciences of the United States of Americs,* 77(10), pp. 5754-5758.

Smith, A. G., Luk, N., Newton, R. A., Roberts, D. W., Sturm, R. A., & Muscat, G. E. (2008). Melanocortin-1 receptor signaling markedly induces the expression of the NR4A nuclear receptor subgroup in melanocytic cells. 283(18), pp. 12564-12570.

Ter Laak, M., Brakkee, J., Adan, R., Hamers, F., & Gispen, W. (2003). The potent melanocortin receptor agonist melanotan-II promotes peripheral nerve regeneration and has neuroprotective properties in the rat. *Eur J Pharmacol.,* 462(1-3), pp. 179-183.

Volakilis, N., Kadkhodaei, B., Joodmardi, E., Wallis, K., Panman, L., Silvaggi, J., . . . Perlmann, T. (2010). NR4A orphan nuclear receptors as mediators of CREB-dependent neuroprotection. 107(27), pp. 12317-12322.

Yin, P., Luby, T. M., Chen, H., Etemad-Moghadam, B., Lee, D., Aziz, N., . . . Hedley, M. L. (2003). Generation of expression constructs that secrete bioactive alphaMSH and their use in the treatment of experimental autoimmune encephalitis. *Gene Therapy,* 10, pp. 349-355.

EXAMPLES

Example 1: Systemic NDP-MSH Treatment of Ongoing Experimental Autoimmune Encephalomyelitis (EAE)

To investigate whether NDP-MSH is able to inhibit autoimmunity and inflammation in organs different from the skin, such as the central nervous system (CNS), the mouse model of experimental autoimmune encephalomyelitis (EAE), a T cell-mediated inflammatory autoimmune disease resembling human multiple sclerosis, was used.

Therefore, C57BL/6 mice were actively immunized by subcutaneous injection of myelin oligodendrocyte glycoprotein ($MOG_{35-55}$) emulsified in Complete Freund's Adjuvant at the back skin (day 0). At day 0 and day 2 mice received intraperitoneal injections of 400 ng pertussis toxin and disease development was monitored daily. When mice reached a clinical score of 2-3 (beginning hind limb paralysis, day 12) they were injected intravenously with 5 μg NDP-MSH or an equal amount of PBS every 48 h. Mice treated with NDP-MSH started gaining weight after the first injection of the hormone (right) and recovered from paralysis whereas control animals exhibited a significant weight loss and continued developing severe ascending paralysis (left). All mice were sacrificed at day 17 and analyzed on a cellular and molecular level. Data were obtained from n=12 mice in each group is depicted, *, p<0.05 versus PBS-treated controls.

Example 2: Effect of NDP-MSH on Inflammation in the CNS Myelination Status of Neurons Brain tissue from mice treated with NDP-MSH or PBS at day 17 post immunization obtained from Ex. 1 was analyzed. H&E staining showed substantial numbers of mononuclear, pro-inflammatory cells infiltrating the brain of PBS-treated controls whereas almost no cell infiltrates were detectable in brain tissue from NDP-MSH treated animals. One representative overview (A) as well as a sectional enlargement (B) is depicted for each group. (C) Myelin staining using luxol fast blue showed complete demyelination of the brain in PBS-treated mice as well as tremendous re-myelination in NDP-MSH treated animals. (representative D) Dramatically reduced expression of markers associated with tissue inflammation (RILPL2) and tissue destruction (APP) in the brain of NDP-MSH-treated mice compared to PBS-treated controls was observed. One representative image for each group is shown. Immunofluorescence staining and histology of the brain tissue revealed reduced numbers of pro-inflammatory mononuclear cells infiltrating the brain of NDP-MSH treated mice compared to PBS treated controls. Moreover, the expression of markers characteristic for CNS inflammation or neurodegeneration, like RILPL2 or APP, respectively were significantly reduced in NDP-MSH treated mice versus controls. Besides reducing the CNS inflammation NDP-MSH also induced the re-myelination of neurons as evidenced by luxol fast blue staining, which detects myelin.

Example 3: Numbers of Pathogenic Th1 and Th17 Cells in the CNS after NDP-MSH Treatment In support of the beneficial effects of NDP-MSH on the progression of ongoing EAE, flow cytometry of CNS revealed decreased levels of pathogenic Th1 as well as Th17 effector cells in NDP-MSH treated mice versus PBS treated controls.

Reduced numbers of pathogenic Th1 and Th17 cells in the CNS from NDP-MSH treated mice compared to PBS-treated controls. At day 17 post immunization brain and spinal cord were isolated from PBS- and NDP-MSH-treated mice and single cell suspensions were prepared using density gradient centrifugation. Subsequently, cells were analyzed by multicolor flow cytometry using antibodies against CD4, IL-17, ROR-gt, IFN-g and T-bet. One representative image (left) as well as the statistical evaluation from n=8 mice in each group (right) is depicted, showing a significantly reduced infiltration of Th17 cells (factor 5) and Th1 cells (factor 2) in the CNS from NDP-MSH-treated mice compared to controls. Cells are gated for CD4 and IL-17, ROR-gt, IFN-g as well as T-bet staining was performed after cell permeabilization.

Example 4: NDP-MSH Induces Functional Regulatory T Cells in the CNS by Generating Tolerogenic Dendritic Cells Numbers, phenotype and function of $Foxp3^+$ regulatory T cells (Treg) isolated from brain tissue of NDP-MSH and PBS treated mice as described in Ex. 1 was analyzed at day 17 post immunization by flow cytometry analysis.

Notably, up-regulated levels of $Foxp3^+$ Treg expressing characteristic markers, such as Helios or CTLA-4, were present at higher numbers in brain tissue from NDP-MSH treated mice compared to controls. Of note, these Treg were functional as they efficiently inhibited the proliferation of effector T cells in vitro. Further, the DC phenotype in regional lymph nodes from immunized NDP-MSH and PBS treated mice was analyzed. Interestingly, DC from NDP-MSH injected mice expressed increased levels of PD-L1 or IL-10 and down-regulated typical maturation markers like CD80 and IFN-γ pointing to the induction of tolerogenic DC in MOG$_{35-55}$ immunized and NDP-MSH treated animals.

Example 5: Effects of NDP-MSH on EAE Progression by Signaling Via Melanocortin-1 Receptor To investigate whether the NDP-MSH induced effects on the progression of EAE were mediated via binding to a functional MC-1R, EAE was induced in MC-1R deficient mice with a point mutation in the MC-1R gene resulting in a truncated protein (Roberts et al., 1993). Mice were immunized with MOG$_{35-55}$, injected with pertussis toxin and treated with NDP-MSH or PBS as described in Ex. 1. Subsequently, disease development was monitored over time.

Notably, NDP-MSH treated MC-1R deficient mice developed hind limb paralysis similar to PBS treated controls demonstrating that signaling via a functional MC-1R is essential for the NDP-MSH mediated amelioration of disease. Together, these data indicate that NDP-MSH by binding to MC-1R induces tolerogenic DC and expands functional Treg. These Treg suppress pathogenic Th1 and Th17 effector cells during EAE progression. The extensive re-myelination of neurons from NDP-MSH treated mice compared to PBS injected controls furthermore suggests a neuroprotective effect of NDP-MSH.

Example 6: Effects of NDP-MSH in a Spontaneous EAE Model (Devic Mice)

To characterize the effects of NDP-MSH in a spontaneous EAE model Devic mice were used. Devic mouse mutants express transgenic T- and B-cell receptors specific for MOG and spontaneously develop EAE at the age of 4-5 weeks (Bettelli et al., 2006).

Starting at the age of 38 days when mice reached a clinical score of 7 (severe hind limb paralysis) animals were injected intravenously with 5 μg NDP-MSH every other day. In total, treatment of mice with NDP-MSH for 3 weeks resulted in a significant amelioration of disease in all animals. Whereas PBS treated control mice showed a considerable weight loss and continued developing severe ascending paralysis, mice injected with NDP-MSH gained weight and recovered from clinical symptoms of EAE. Part of the mice almost completely recovered from disease. At day 60, NDP-MSH treatment was interrupted and mice were monitored for the onset of clinical symptoms. Notably, even after several weeks without NDP-MSH injection EAE pathology was stable in all animals and no disease recurrence in any of the NDP-MSH treated Devic mice was observed. Together, these data point to a long-lasting neuroprotective effect of NDP-MSH.

Figure 8:
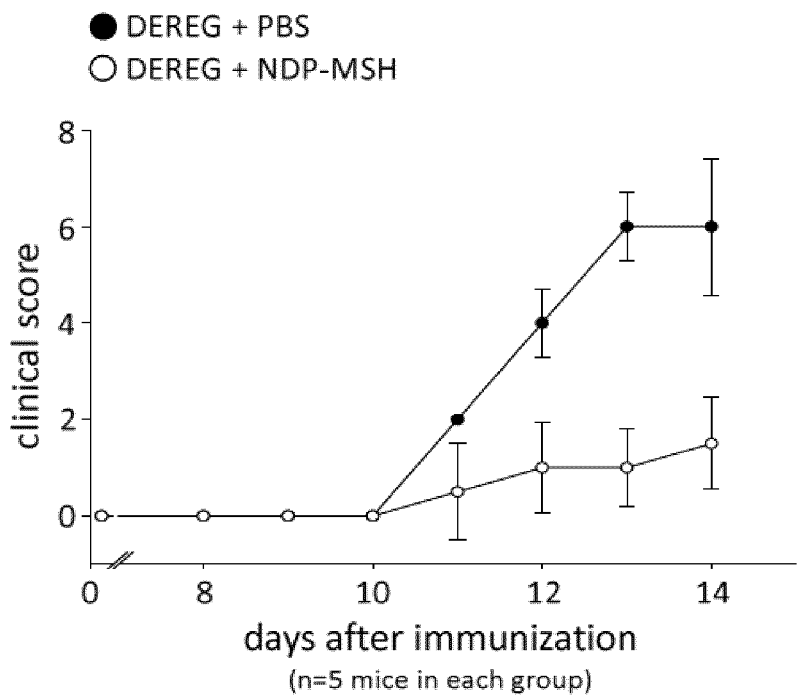
FIG. 8 Effect of NDP-MSH in DEREG mice with induced EAE. Treg were depleted in DEREG mice as described by Lahl et al. (2007) by systemic treatment with diphtheria toxin. Subsequently, EAE was induced as described in FIG. 1. 5 µg NDP-MSH were injected intravenously every 48 hours and disease progression was monitored over time.
Figure 9:
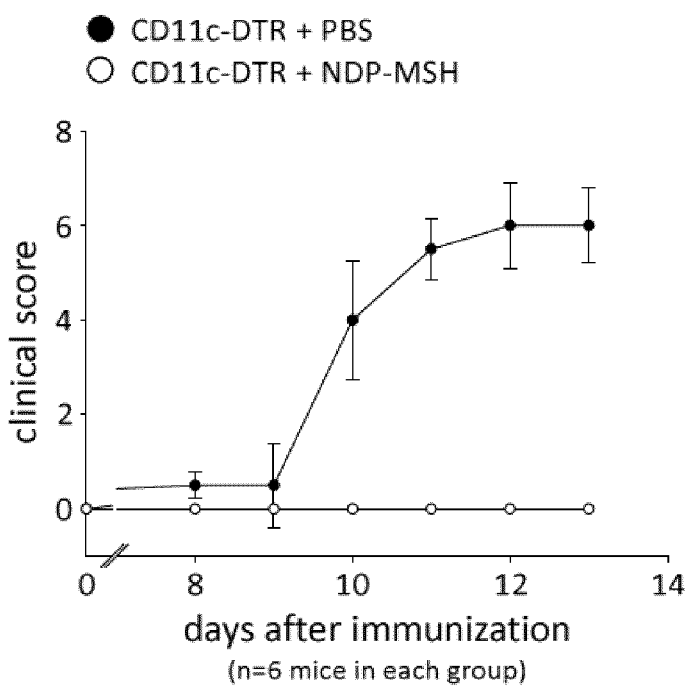
FIG. 9 Effect of NDP-MSH in C11c-DTR mice with induced EAE. DC were depleted in C11c-DTR mice as described by Hochweller et al. (2008) by systemic treatment with diphtheria toxin. Subsequently, EAE was induced as described in FIG. 1. 5 µg NDP-MSH were injected intravenously every 48 hours and disease progression was monitored over time.
Figure 10:
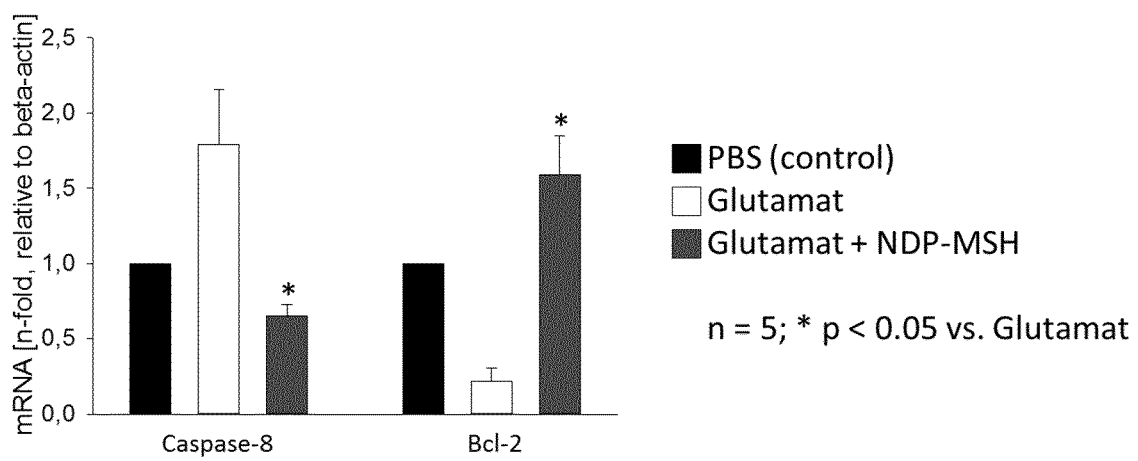
FIG. 10 Expression of pro-apoptotic (caspase-8) and anti-apoptotic (Bcl-2) genes in primary mouse neurons after treatment with 50 µm Glutamat or 50 µM Glutamat+1 nM NDP-MSH. Primary murine neurons were stimulated with glutamate which results in apoptosis (increased expression of pro-apoptotic caspase-8 and a reduced expression of anti-apoptotic Bcl-2 relative to PBS-treated controls). Addition of NDP-MSH to the glutamate-stimulated neuron cultures prevents induction of cell death (reduced expression of pro-apoptotic caspase-8, increased expression of anti-apoptotic Bcl-2).

Example 7: Effect of NDP-MSH on EAE in Mice after Depletion of Regulatory T Cells or Dendritic Cells To further elucidate the mode of action of NDP-MSH on EAE, Treg and DC were depleted in DEREG (Lahl et al., 2007) or CD11c-DTR mice (Hochweller et al. 2008), respectively by systemic treatment with diphtheria toxin. Subsequently, EAE was induced as described in Ex. 1. Intravenous injection of 5 μg NDP-MSH every 48 hours resulted in reduced disease severity in NDP-MSH treated DEREG mice (FIG. 8) and prevented disease onset in CD11c-DTR mice (FIG. 9) even in the absence of Treg or DC. These data demonstrate that not only Treg and tolerogenic DC, which are induced by NDP-MSH, account for the observed effects in EAE but in contrast indicate a strong neuroprotective role of NDP-MSH in inflammatory as well as neurodegenerative disorders of the CNS.

---

The invention claimed is:

1. A method of ameliorating the symptoms of inflammatory and/or neurodegenerative disorders of the Central Nervous System (CNS) in a subject in need thereof comprising administering NDP-MSH or pharmaceutically acceptable salts thereof, wherein the inflammatory and/or neurodegenerative disorder of the CNS is acute disseminated encephalomyelitis (ADEM).

2. The method of claim 1, wherein the method comprises therapeutic and/or a therapeutic prophylactic treatment.

3. The method of claim 1, wherein the method has an anti-inflammatory and/or neuroprotective effect.

4. The method of claim 1, wherein the subject is a mammal.

5. The method of claim 1, wherein NDP-MSH or a pharmaceutically acceptable salt thereof is chemically modified.

6. The method of claim 1, wherein NDP-MSH is administered during relapse, progression and/or remission.

7. The method of claim 1, wherein NDP-MSH or a pharmaceutically acceptable salt thereof is administered intravenously.

8. The method of claim 1, wherein 1-500 µg/kg of body weight of NDP-MSH or the pharmaceutically acceptable salt is administered.

9. The method of claim 1, wherein NDP-MSH is administered in repeatedly in intervals of 12-72 hours.

10. A method of ameliorating the symptoms of inflammatory and/or neurodegenerative disorders of the Central Nervous System (CNS) in a subject in need thereof comprising administering NDP-MSH or pharmaceutically acceptable salts thereof, wherein the inflammatory and/or neurodegenerative disorder of the CNS is acute hemorrhagic leukoencephalitis (AHLE).

11. The method of claim 10, wherein the method comprises therapeutic and/or a therapeutic prophylactic treatment.

12. The method of claim 10, wherein the method has an anti-inflammatory and/or neuroprotective effect.

13. The method of claim 10, wherein the subject is a mammal.

14. The method of claim 10, wherein NDP-MSH or a pharmaceutically acceptable salt thereof is chemically modified.

15. The method of claim 10, wherein NDP-MSH is administered during relapse, progression and/or remission.

16. The method of claim 10, wherein NDP-MSH or a pharmaceutically acceptable salt thereof is administered intravenously.

17. The method of claim 10, wherein 1-500 µg/kg of body weight of NDP-MSH or the pharmaceutically acceptable salt is administered.

18. The method of claim 10, wherein NDP-MSH is administered in repeatedly in intervals of 12-72 hours.

* * * * *